(12) United States Patent
McFadden et al.

(10) Patent No.: US 8,976,926 B2
(45) Date of Patent: Mar. 10, 2015

(54) PORTABLE 3-DIMENSIONAL X-RAY IMAGING SYSTEM

(75) Inventors: Michael J. McFadden, San Antonio, TX (US); Jeffrey L. Boehme, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 718 days.

(21) Appl. No.: 13/244,372

(22) Filed: Sep. 24, 2011

(65) Prior Publication Data

US 2013/0077739 A1 Mar. 28, 2013

(51) Int. Cl.
*G01N 23/083* (2006.01)
*G01N 23/04* (2006.01)
*A61B 6/02* (2006.01)

(52) U.S. Cl.
CPC .............. *G01N 23/04* (2013.01); *G01N 23/046* (2013.01); *A61B 6/027* (2013.01); *A61B 6/025* (2013.01)
USPC ................................ 378/25; 378/22; 378/197

(58) Field of Classification Search
CPC ...... A61B 6/025; A61B 6/027; A61B 6/4452; A61B 6/4458; G01N 23/046; G01N 23/083; G01N 2223/301; G01N 2223/308; G01N 2223/639; G06T 11/003; G06T 11/005; G06T 15/06
USPC ................................ 378/21, 22, 25, 196, 197
See application file for complete search history.

(56) References Cited

U.S. PATENT DOCUMENTS

| | | | |
|---|---|---|---|
| 6,940,943 B2 * | 9/2005 | Claus et al. ..................... | 378/27 |
| 7,029,174 B1 | 4/2006 | Mattingly et al. | |
| 7,103,137 B2 | 9/2006 | Seppi et al. | |
| 7,110,490 B2 * | 9/2006 | Eberhard et al. ................ | 378/23 |
| 7,177,390 B2 * | 2/2007 | Martin et al. .................... | 378/25 |
| 7,218,702 B2 * | 5/2007 | Mistretta et al. ................ | 378/21 |
| 7,336,765 B1 | 2/2008 | Amiton et al. | |
| 7,356,113 B2 * | 4/2008 | Wu et al. ......................... | 378/27 |
| 7,466,795 B2 * | 12/2008 | Eberhard et al. ................ | 378/37 |
| 7,505,562 B2 | 3/2009 | Dinca et al. | |
| 7,558,366 B2 * | 7/2009 | Barth et al. ..................... | 378/27 |
| 8,254,518 B2 * | 8/2012 | Paidi et al. ...................... | 378/22 |
| 2005/0251010 A1 * | 11/2005 | Mistretta et al. .............. | 600/407 |
| 2007/0165922 A1 * | 7/2007 | Webber et al. ................ | 382/128 |
| 2009/0296881 A1 * | 12/2009 | Hornig ............................ | 378/37 |
| 2011/0019797 A1 | 1/2011 | Morton | |
| 2012/0201345 A1 * | 8/2012 | Paidi et al. ........................ | 378/9 |

* cited by examiner

*Primary Examiner* — Thomas R Artman
(74) *Attorney, Agent, or Firm* — Chowdhury & Georgakis, P.C.; Ann C. Livingston

(57) ABSTRACT

An x-ray imaging system and method for providing three-dimensional data representing the contents of an object. An x-ray source and x-ray screen are used to acquire multiple x-ray images of the object from different perspectives. The different perspectives are obtained by placing the x-ray source at one end of a moveable arm. These images are processed by back-projecting each perspective image at known distances between the object and the x-ray source, and superimposing the back-projected images at each distance, thereby providing a set of image slices of the object along the z-axis.

16 Claims, 7 Drawing Sheets

PORTABLE 3-DIMENSIONAL X-RAY IMAGING SYSTEM

GOVERNMENTAL RIGHTS

This invention was made with United States Government support under Contract No. N00014-11-C-0142 awarded by the Office of Naval Research. The Government has certain rights in this invention.

TECHNICAL FIELD OF THE INVENTION

This invention relates to x-ray imaging systems and methods, and more particularly to using an x-ray imaging system to provide three-dimensional information about the contents of an opaque object.

BACKGROUND OF THE INVENTION

Explosive Ordnance Disposal (EOD) personnel, often called "bomb squads," are charged with the task of investigating and disposing of unexploded ordnance (UXO) in both domestic and military settings. Most UXO is detonated in-place, using a "disrupter" projectile fired at the ignition source of the ordnance. However, in some cases, such as when the UXO is an improvised nuclear device or when it endangers a high-value asset, it cannot be detonated in-place. In these situations, EOD personnel are tasked with diffusing the UXO without detonation, which can be challenging, especially for IEDs equipped with booby-trap triggers and decoy detonators.

One of the tools used by EOD personnel to aid in both detonation-in-place and diffusing is an x-ray imaging system, such as the SAIC RTR-4 system. For detonation-in-place, a single X-ray image can provide sufficient information for aiming the disruptor projectile. However, for diffusing, EOD personnel often find it necessary to view multiple x-ray images from numerous perspectives. Taking images from multiple perspectives enables EOD personnel to estimate the relative locations of components within the IED to ensure entry into the IED at the correct locations.

Unfortunately, collecting multiple images for several perspectives requires physically moving the source, and sometimes the imaging screen. This can significantly increase the time-on-target for EOD personnel, which is undesirable. Furthermore, even when a series of perspectives is acquired, determining the z-position of components within the IED is difficult.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

As indicated in the Background, x-ray images are notoriously "flat". They are not images, per se, but rather projections, similar to shadows. An x-ray image provides a two-dimensional view of x-axis and y-axis positions, but provides very little z-axis (depth) information.

The following description is directed to using x-ray images to determine three-dimensional location information about components contained within an object having an opaque enclosure, such as an improvised explosive device (IED). As explained below, an x-ray source is mounted to a moveable arm, which moves through a number of positions to collect multiple images from multiple perspectives. Each of these multiple images is a conventional two-dimensional x-ray projection. However, the collection of images is processed to provide depth information about the contents of the object.

In this manner, the system and method described herein determine the three-dimensional positions of components within an object. The components' x-y as well as z-axis (depth) positions are determined. The information may be presented in various ways, such as in the form of a three-dimensional computer model of the object. In the case of an IED, this information will enable safe access into the IED so that it can be defused.

Figure 1:
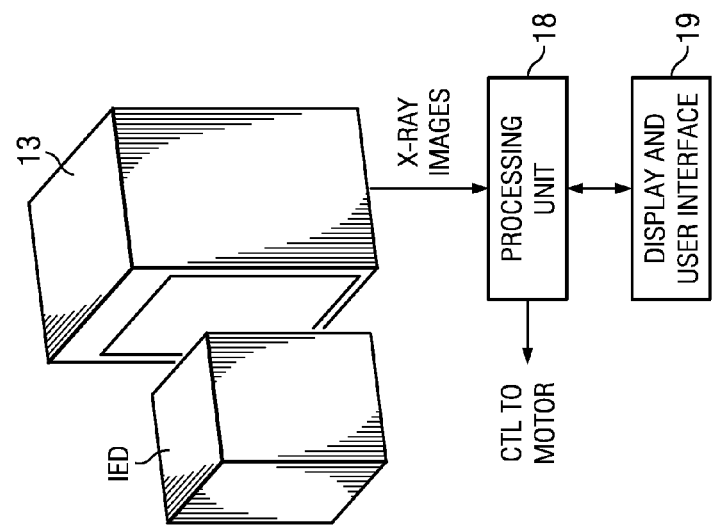
FIG. 1 illustrates an x-ray imaging system for providing three-dimensional data representing the contents of an opaque object.
Figure 1:
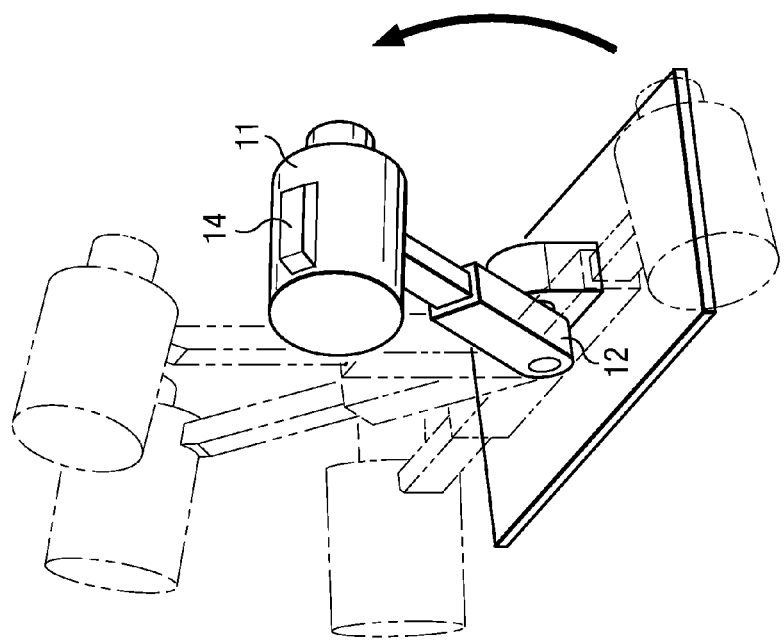

FIG. 1 illustrates an x-ray imaging system for providing three dimensional data about the contents of an opaque object. For purposes of example, the object is assumed to be an IED. An x-ray source 11 in front of the object is mounted on a pivot arm 12. The pivot arm 12 can be moved in known increments to step the x-ray source 11 through multiple positions.

In the embodiment of FIG. 1, the pivot arm 12 moves the x-ray source 11 in a vertical arc, that is, an arc in the same plane as the x-ray sensor screen 13. The x-ray source 11 is pointed down a cone angle towards the center of screen 13, which is placed behind the object under investigation.

The motion of the pivot arm 12, as well as the tilt of the x-ray source 11 toward the object, can be performed manually or automated. In more sophisticated embodiments, the pivot arm 12 may be attached to a robot, which performs all or some of the re-positioning tasks described herein.

Figure 2:
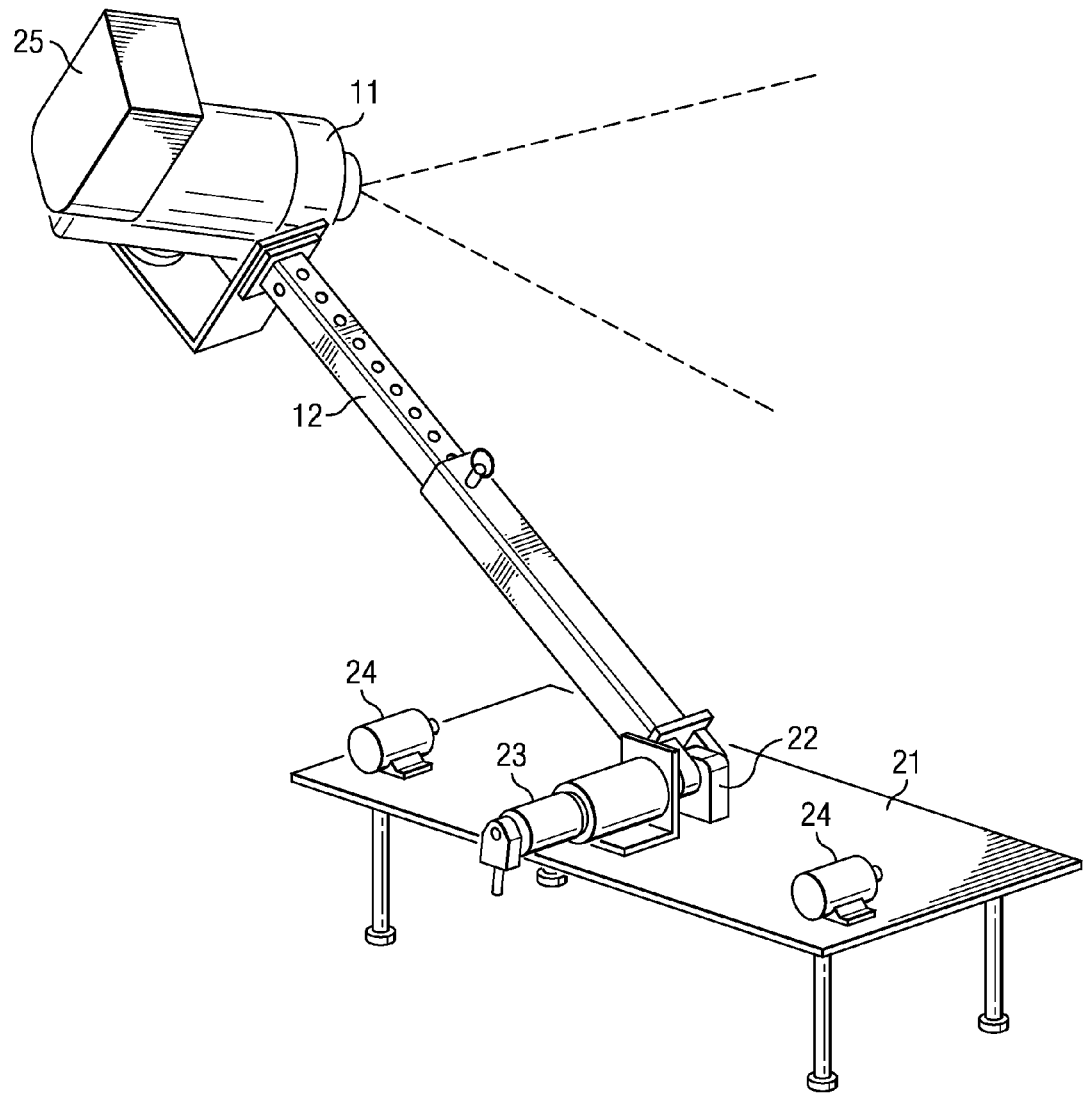
FIG. 2 illustrates a motorized embodiment of the x-ray source and pivot arm of the system of FIG. 1.

FIG. 2 illustrates a motorized embodiment of the x-ray source 11 and pivot arm 12. A base 21 provides secure support for the pivot arm 12 and x-ay source 11, and is typically placed on the ground or floor. A hinged attachment mechanism 22 allows the pivot arm 12 to travel through an arc. Typically, the range of motion will be 180 degrees. A servo motor 23 controls the position of the pivot arm 12 to step it through multiple positions on its arc. This configuration allows the x-ray source 11 to be placed in any position along the arc.

The x-ray source 11 is mounted on the pivot arm 12 so that its tilt may be re-positioned to point toward the center of the x-ray sensor screen 13. Its aperture is aligned to the pivot arm axis, which helps to provide accurate arc positions. Lasers 24 mounted on the base 21 are used to align the pivot axis with the center of the sensor screen 13 and to ensure that the plane of the pivot arm sweep is approximately parallel to the plane of the screen 13. A motor 25 may be used in automated versions of the system, to control the tilt of the x-ray source.

If the motion of pivot arm 12 is automated, such as with motor 23, processing unit 18 controls the motion of pivot arm 12 by generating control signals to the motor. Likewise, adjustment of the field of view of x-ray source 11 may also be automated and controlled by processing unit 18 with control signals to motor 25.

Also, processing unit 18 may be programmed to perform all or part of the image processing described below. To this end, it is assumed that processing unit 18 is in data communication with sensor screen 13 to receive x-ray images, and has appropriate hardware and software for performing the image processing tasks described herein. All or part of processing unit 18 may be remote from the rest of the x-ray imaging system.

A display and user interface unit 19 is in data communication with processing unit 18. Unit 19 allows an operator to control the motion of pivot arm 12 and x-ray source 11, and to view the results of the processing.

Optionally, pivot arm 12 may be telescoping. The ability to shorten the length of pivot arm 12 enables the x-ray system to break down for compact stowage. Also, a longer arm length may be desirable for larger objects or for a longer distance between the object and the x-ray source 11.

In operation, the x-ray sensor screen 13 is placed behind the object. The pivot arm 12 is placed in front of the object, with the x-ray source 11 pointed toward the center of the screen 13. The pivot arm 12 is stepped through a series of discrete positions and a set of x-ray projection images is collected.

Figure 3A:
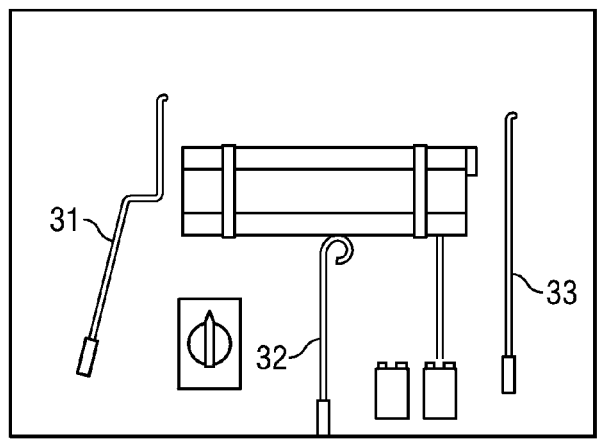
FIGS. 3A, 3B and 3C illustrate three x-ray projection images of a simulated IED, each obtained from a different perspective of the x-ray source.
Figure 3B:
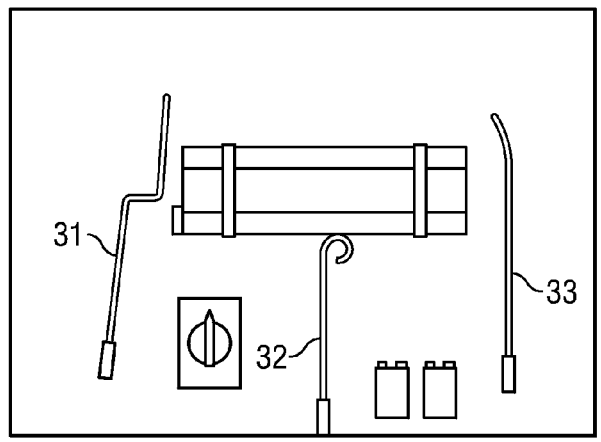
Figure 3C:
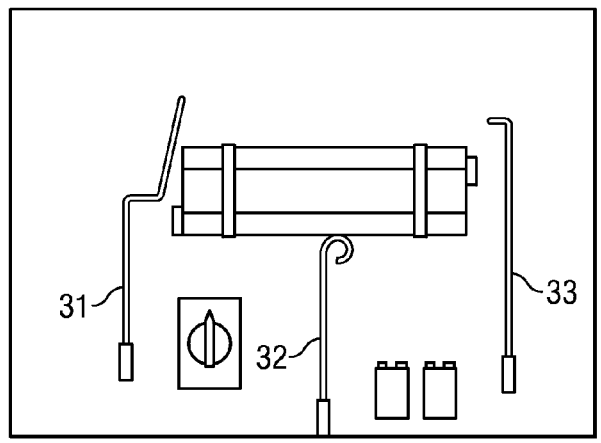

FIGS. 3A, 3B and 3C illustrate three x-ray projection images of a simulated IED, each obtained at a different perspective of the x-ray source 11. The simulated IED has various components, including three booby trap triggers 31-33.

In an actual test, these images were a subset of thirteen images taken at 15-degree increments from 0 to 180 degrees. FIGS. 3A, 3B and 3C are of projections at 0, 90 and 180 degrees, respectively.

The projection image collected at each position of the x-ray source 11 provides a different perspective on the contents of the object. The set of images from the different perspectives is referred to herein as the "perspective images".

Although not readily apparent from the images, because of the different perspectives, the components within the object are shifted in each image. This shifted feature of the perspective images is used to extract z-dimensional information from a set of processed images.

Specifically, each perspective image is processed to achieve back-projections in the direction of the source along a series of discrete depth positions. This is achieved by mathematically shifting and shrinking each projection image at known increments along the z-axis in the direction of the source x-ray. The result is a set of back-projection images for each perspective image.

Next, the resized-and-shifted back-projections from all images are superimposed (converged) at each position in z. The effect is that components of the object that exist at a particular z-location will coincide in x and y and thus achieve an additive effect. The result is a set of 2-D convergence images of the 3-D object in the z-dimension.

The 2-D convergence images can be presented as a sequence of convergence frames, where each frame represents a 2-D slice in the third (z) dimension. A threshold operation may be used to select the elements that are present in each convergence frame.

Figure 4A:
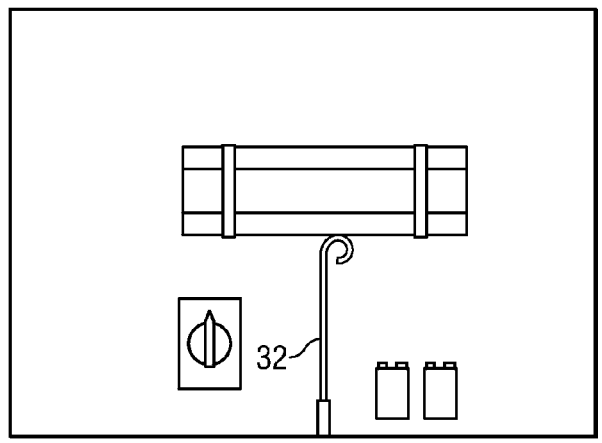
FIGS. 4A, 4B and 4C illustrate an example of three convergence slices at various planes of the z dimension.
Figure 4B:
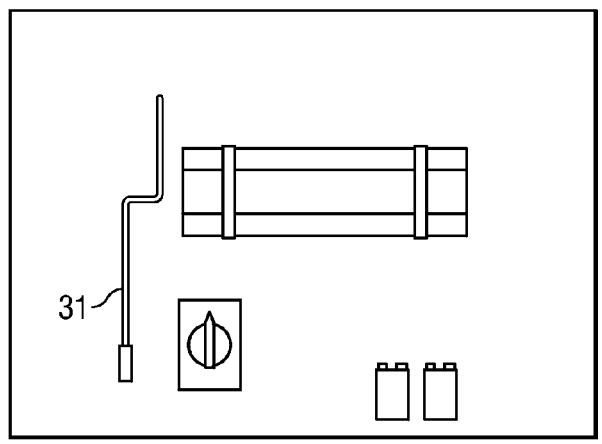
Figure 4C:
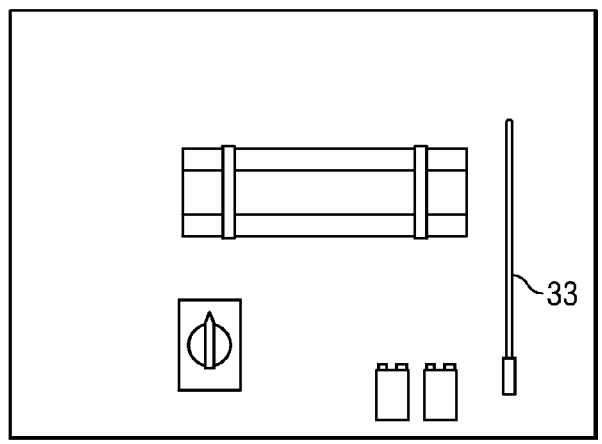

FIGS. 4A, 4B and 4C illustrate an example of three convergence slices at various planes of the z dimension (depth). The components in the images that are more sharply resolved are located in the z-plane associated with each image. Thus, the z-axis location of components inside the object can be determined.

Of particular interest in the IED example of this description is the fact that there are three booby-trap triggers 31-33 in this simulated IED. Each booby-trap trigger can be located at its respective depth in the IED, allowing the EOD technician to enter the device with confidence while avoiding inadvertent detonation.

The pivot arm length and angle and the pivot-point location relative to the center of the sensor screen are important for determining the position of the source relative to the screen, which is used by the processing software to extract the z-dimension information.

Figure 5:
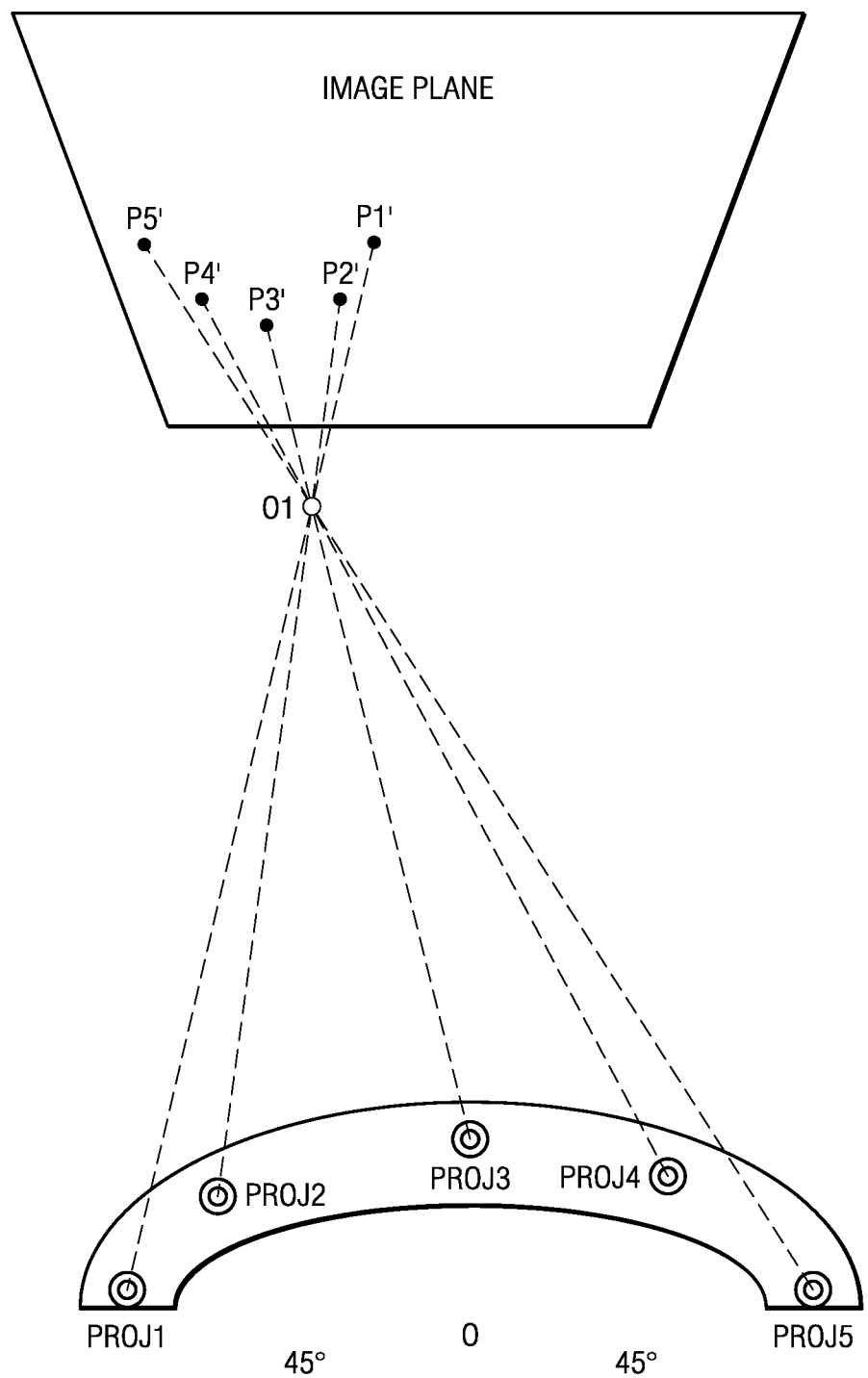
FIGS. 5 and 6 illustrate the convergence concept of the method of providing three-dimensional data representing the location of contents of an opaque object.
Figure 6:
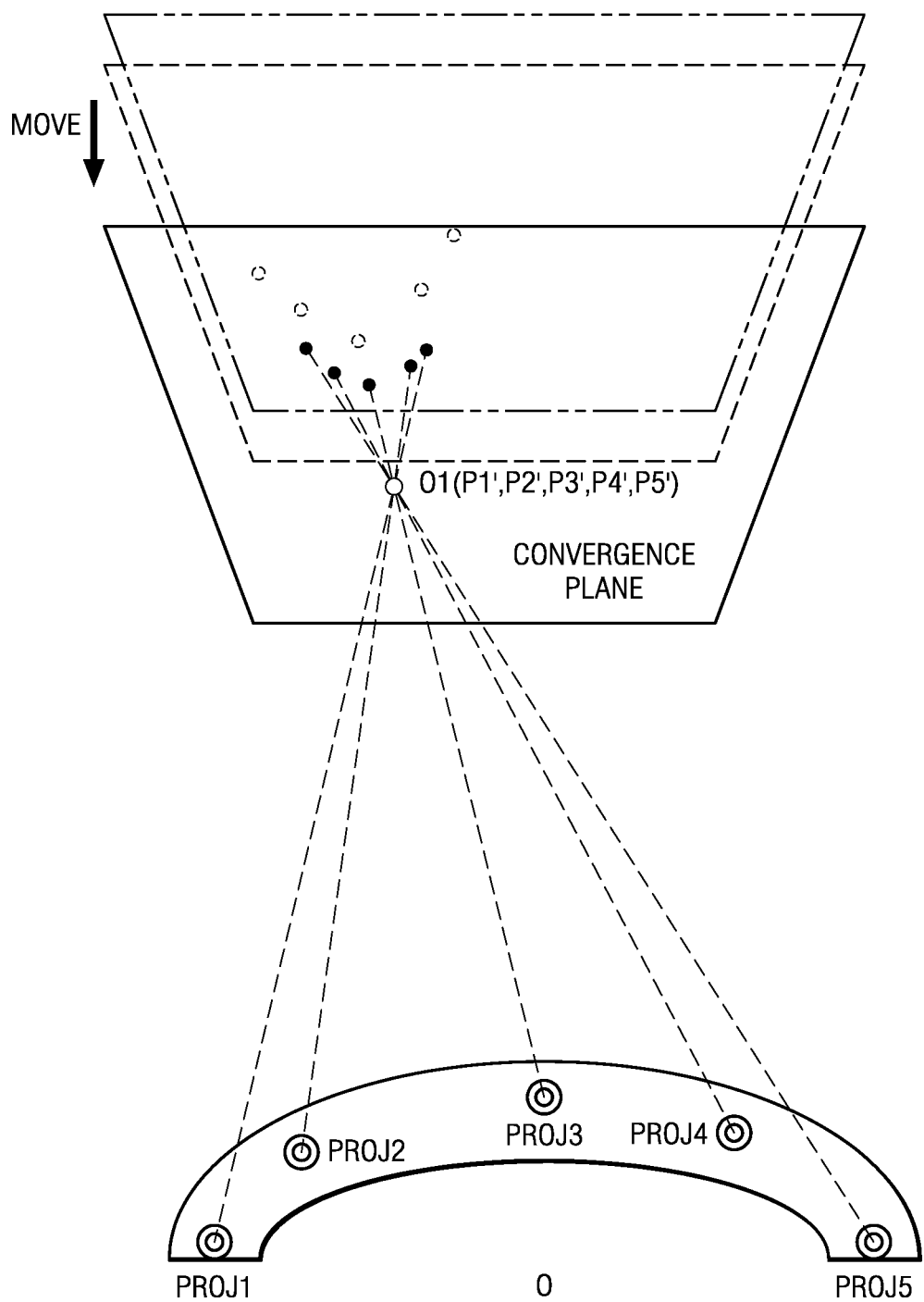

FIGS. 5 and 6 illustrate the convergence concept of the above-described method. As shown in FIG. 5, when the x-ray source is stepped through five different angular positions in an arc, Point O1 is projected to five different locations in the image plane (x-ray screen 13), namely P1', P2', P3', P4', P5'. It is possible to simulate the effect of moving the image plane in the direction of the source by back-projecting and overlaying the five images. The back projection is done by shifting and shrinking each image according to the geometry that follows from the relative distances and angles between the source and screen, which are different for each of the five projection images.

FIG. 6 illustrates projection of the image plane closer to O1. The five imaging points become closer together. When the projected image plane intersects O1, the 5 imaging points become superimposed. This point of intersection, which occurs at the convergence plane, leads to higher signal levels when the projections are added together. If the image plane is further projected, the five superimposed imaging points diverge again.

Thus, an object in the summed projected images comes into convergence and then diverges again as a consequence of the simulated movement of the image plane in the direction of the source. When convergence is at its peak, the object has its highest intensity value.

The output of the process is a three-dimensional data volume that contains location information about the components in the object. The data volume can be presented as a sequence of data slices in the z-dimension. These data slices can be further presented as frames in a video, or exported as a point cloud to a solid-model rendering software program. Regardless of the specific form of the output, in general terms, the output presents three-dimensional data representing the contents of the object.

Additional processing can be performed to eliminate false results and for edge sharpening. False positives can occur when different objects happen to project to the same location; false negatives can occur when objects have weak signal levels due to illumination or absorbance variations.

In other embodiments, the x-ray imaging system of FIG. 1 could be modified such that the x-ray source 11 is moveable from side to side, or up or down, or in any direction, as long as it provides multiple perspectives from positions that vary in height (y-dimension) and from side-to-side (x-dimension), and those positions are known within a reasonable accuracy. It is important for the processing that the relative position of the x-ray source and x-ray sensor screen are known at every projection. An advantage of moving the x-ray source in an arc is that it provides a simple way to span a number of positions in x and y and provide widely varying perspectives on the object. Assuming a well-designed x-ray system apparatus, these positions can be well known by aligning the base of the system to the x-ray sensor screen and moving the pivot arm at known intervals, say 15 degrees each.

Figure 7:
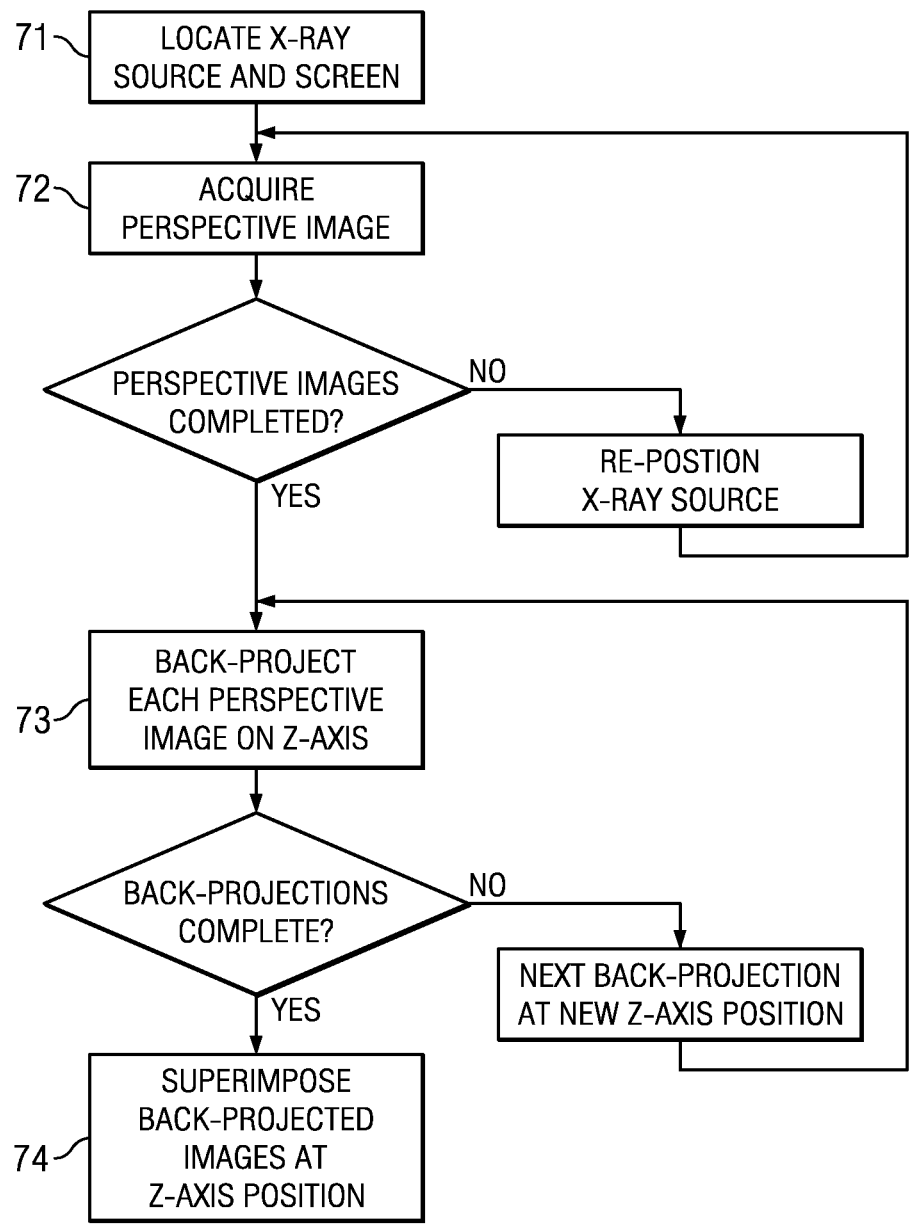
FIG. 7 illustrates the basic steps of a method of providing three-dimensional data representing the location of contents of an opaque object.

FIG. 7 illustrates the basic steps of a method of providing three-dimensional data representing the contents of an object. The system of FIG. 1 may be used to implement the method, with the positioning of the x-ray source 11 and the x-screen 12 being performed either manually or mechanically. Specifically, the initial position of the system, the movement of the pivot arm, and the tilt of the x-ray are all operations that may be performed manually or by robot or motor.

Step 71 is the initial positioning of the x-ray source 11 and the x-ray screen 13. As explained above, the object under inspection is placed in front of the screen 13, and the pivot arm 12 and x-ray source 11 are positioned so that suitable perspective views can be acquired.

Step 72 is acquiring perspective images from a number of different positions of the pivot arm 12. As explained above, this step can be performed by moving the pivot arm 12 in a vertical arc. The direction of movement of the x-ray source 11 is not important so long as good perspectives are obtained, and each position of the x-ray source relative to the object is known. Step 72 is repeated until a desired number of perspective images is obtained.

Step 73 is processing the perspective images to obtain back-projection images. As explained above, this is accomplished by shifting and re-sizing each perspective image at known locations along the z-axis. Step 73 is repeated for each perspective image.

Step 74 is superimposing the back-projection images at each location on the z-axis. As explained above, at each z-axis location, the back-projection images are superimposed. The result is an image slice at each z-axis location. Components within the object that are in the same plane in the object will be more intensely illuminated. Further processing can be performed to estimate the location of the component within the object in three-dimensional space. As further explained above, the results of the processing can be presented to the operator in various forms.

In an enhanced version of the above method, the x-ray system is used to acquire projection images by re-positioning the system to acquire images from a second orientation of the x-ray system. Typically, the second orientation is in a different plane. For example, as described above, the x-ray imaging system is positioned to collect a series of images in a first arc, such as a vertical arc. Then, the system is re-positioned to collect a series of images in a second vertical arc, such as one 90 degrees from the first arc. Thus, the two arcs of the x-ray source are offset, typically orthogonally. This "multiple orientation" method provides improved three-dimensional data about front and backs of the contents of the object. Once acquired, the projection images from all x-ray source positions are processed (back-projected and superimposed) as described above.

The above-described method allows an EOD technician to spend little or no time-on-target while assessing the IED. In practice, a robot could be used to place the screen and pivot arm. A collection of x-ray images at multiple angles can be quickly acquired. The processing to create the depth data of the object is also fast. It is expected that the images can be acquired in less than five minutes and that the processing can be performed in less than two minutes.

What is claimed is:

1. An x-ray imaging system for providing three-dimensional data representing the contents of an object, comprising:
    an x-ray source;
    a moveable arm having a fixed end and a free end, the free end being attached to the x-ray source;
    an x-ray screen operable to detect x-ray images of the object when the object is placed between the x-ray source and the x-ray screen;
    wherein the arm is moveable to provide different positions of the x-ray source, thereby providing different perspective images to the x-ray screen;
    wherein the arm travels in a vertical arc in a plane parallel to the x-ray screen;
    wherein the x-ray source is moveable, at each position of the arm, to direct the x-ray aperture toward the center of the x-ray screen;
    a processing unit operable to receive a set of x-ray perspective images from the x-ray screen, each perspective image acquired from a different position of the x-ray source; and to apply a back projection algorithm to the set of x-ray perspective images, thereby providing a set of image slices of the object.

2. The system of claim 1, wherein the arm is moveable by means of a motor.

3. The system of claim 1, wherein the x-ray source is moveable by means of a motor.

4. The system of claim 1, wherein the processor is further programmed to provide a three-dimensional model display of the object.

5. The system of claim 1, wherein the arm is mounted on a base, the base having one or more lasers for aligning the arm to the object.

6. The system of claim 1, wherein the arm moves in a sequence of equal steps through an arc.

7. The system of claim 1, wherein the arm is telescoping.

8. The system of claim 1, wherein the arm is attached to a robot.

9. A method of using an x-ray imaging system to provide three-dimensional data representing the contents of an object, comprising:
    placing the object between the x-ray source and the x-ray screen;
    using the x-ray source and the x-ray screen to acquire multiple perspective images from multiple perspectives of the x-ray source;
    wherein the multiple perspective images are acquired by placing the x-ray source at one end of a moveable arm and moving the arm to different positions;
    wherein the arm travels in a vertical arc in a plane parallel to the x-ray screen;
    wherein the x-ray source is moveable, at each position of the arm, to direct the x-ray aperture toward the center of the x-ray screen;
    back-projecting the perspective images,
    thereby providing a set of image slices of the object.

10. The method of claim 9, wherein the arm is moveable by means of a motor.

11. The method of claim 9, wherein the x-ray source is moveable by means of a motor.

12. The method of claim 9, wherein the processor is further programmed to provide a three-dimensional model display of the object.

13. The method of claim 9, wherein the arm moves in a sequence of equal steps through an arc.

14. The method of claim 9, wherein the arm is telescoping.

15. The method of claim 9, wherein the steps of using the x-ray source and x-ray screen to acquire multiple perspective images, back-projecting, and superimposing are performed by acquiring a first set of perspective images in a first orientation of the arm and screen followed by re-positioning the arm and screen to acquire perspective images from a second orientation of the arm and screen.

16. The method of claim 15, wherein the arm and screen are re-positioned such that the arm moves in two orthogonal arcs.

* * * * *